United States Patent

[19]

Cerwin

[11] 4,089,409
[45] May 16, 1978

[54] PACKAGE FOR MULTISTRAND SURGICAL SUTURES

[75] Inventor: Robert J. Cerwin, Pittstown, N.J.

[73] Assignee: Ethicon, Inc., Somerville, N.J.

[21] Appl. No.: 765,579

[22] Filed: Feb. 4, 1977

[51] Int. Cl.² ............................................. A61L 17/02
[52] U.S. Cl. .................................. 206/63.3; 206/388;
206/491; 128/335.5; 229/17 R; 229/40
[58] Field of Search ..................... 206/63.3, 491, 353,
206/392, 388; 128/335.5; 242/174, 159; 229/17 R, 40

[56] References Cited

U.S. PATENT DOCUMENTS

| | | | |
|---|---|---|---|
| 2,619,226 | 11/1952 | Adams | 206/491 |
| 2,895,210 | 7/1959 | Hubbard | 206/63.3 |
| 3,206,018 | 9/1965 | Lewis et al. | 206/63.3 |
| 3,280,971 | 10/1966 | Regan, Jr. | 206/63.3 |
| 3,444,994 | 5/1969 | Kaepernik et al. | 206/63.3 |
| 3,487,917 | 1/1970 | Shave et al. | 206/63.3 |
| 3,759,376 | 9/1973 | Lisowski | 206/63.3 |
| 3,939,969 | 2/1976 | Miller et al. | 206/63.3 |

FOREIGN PATENT DOCUMENTS

| | | | |
|---|---|---|---|
| 585,786 | 10/1933 | Germany | 206/353 |
| 667,379 | 9/1964 | Italy | 242/159 |

*Primary Examiner*—William Price
*Assistant Examiner*—Joseph M. Moy
*Attorney, Agent, or Firm*—Wayne R. Eberhardt

[57] ABSTRACT

A package for multiple strands of surgical sutures which provides for delivery of individual suture strands. The sutures are aligned into a bundle of substantially parallel strands and the bundle is wound in the form of a coil comprising a series of contiguous, overlapping convolutions, each convolution being laterally displaced from adjacent convolutions and disposed in sequence from one end of the suture to the other. The desired suture coil configuration is conveniently obtained by winding the suture bundle around two vertical winding pins in an upwardly spiraling pattern with successive loops being displaced laterally along the pins. The wound suture is packaged in a suture folder which is adapted to maintain the suture bundle in its wound configuration with one end of the suture bundle extending from the folder whereby individual suture strands may be grasped and withdrawn from the package.

19 Claims, 7 Drawing Figures

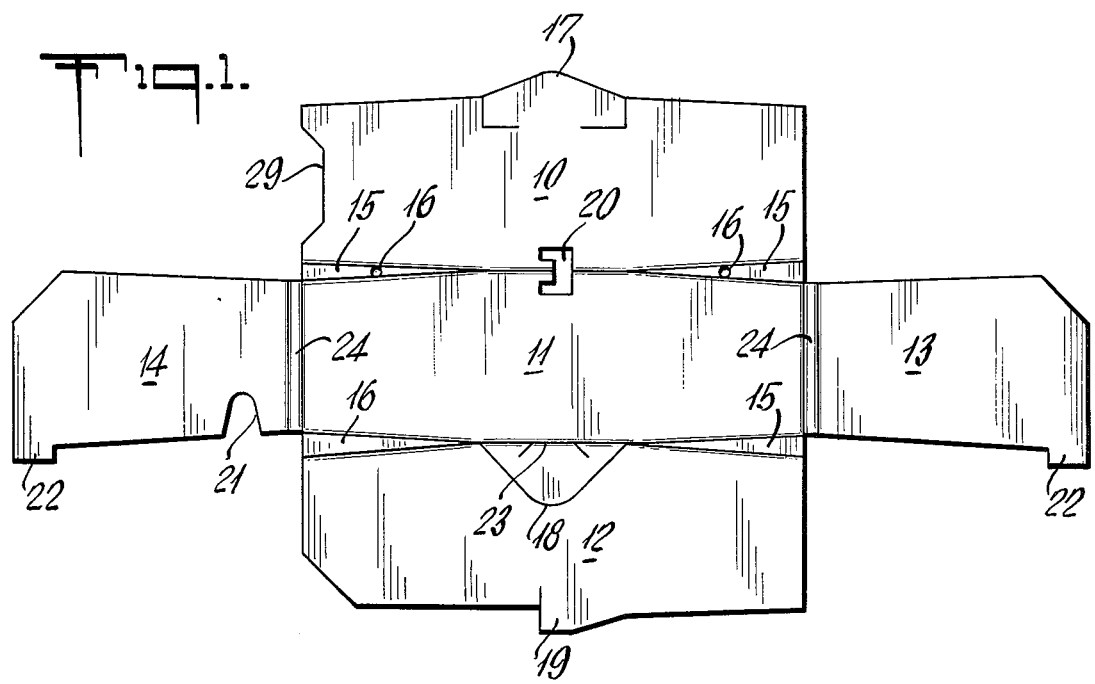
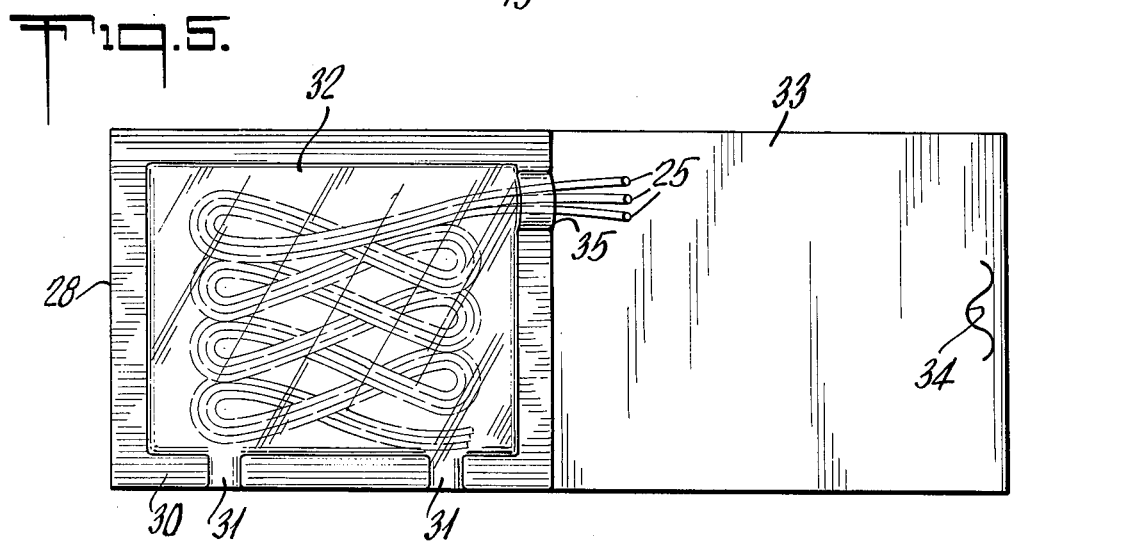
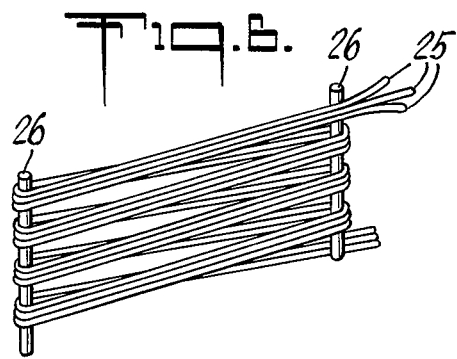
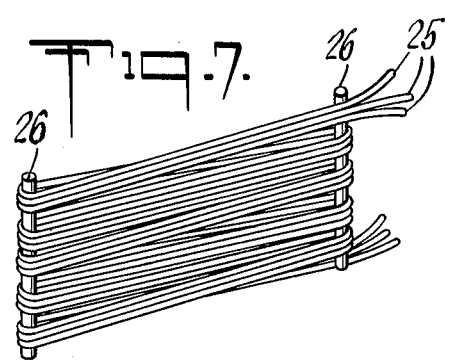

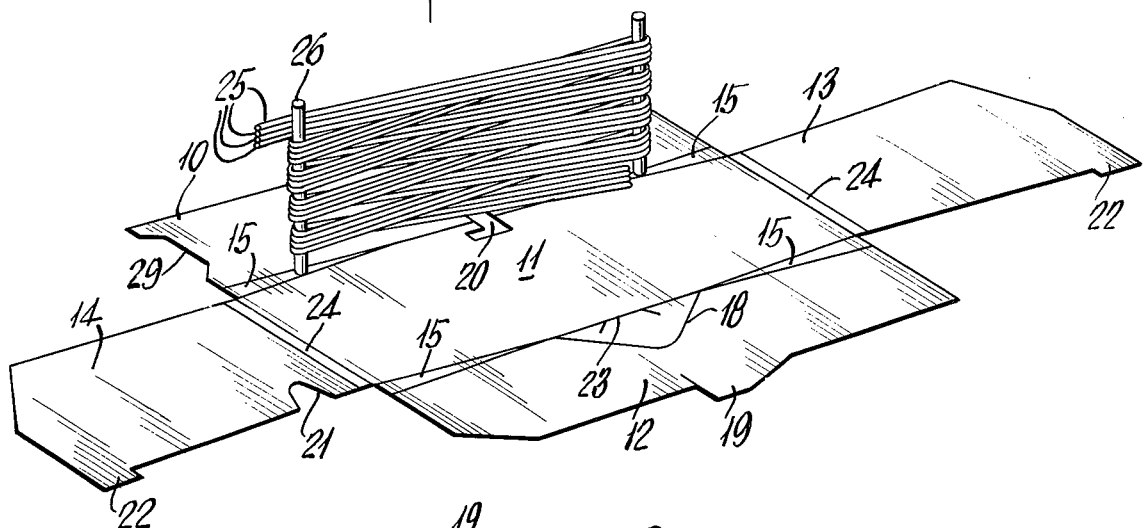
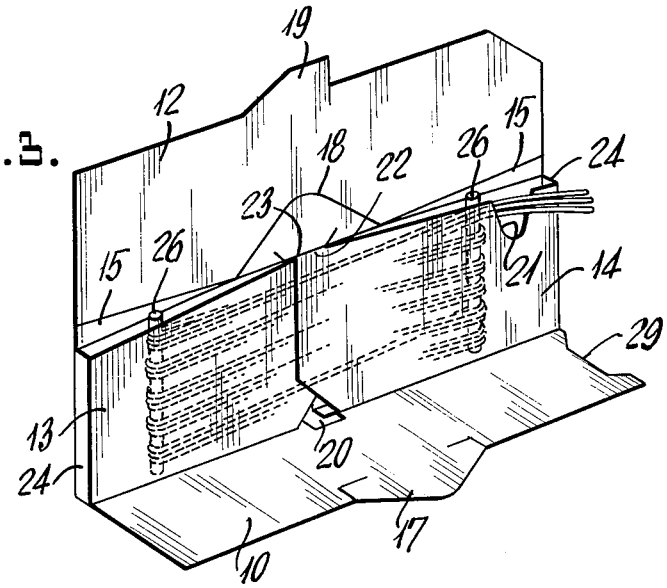
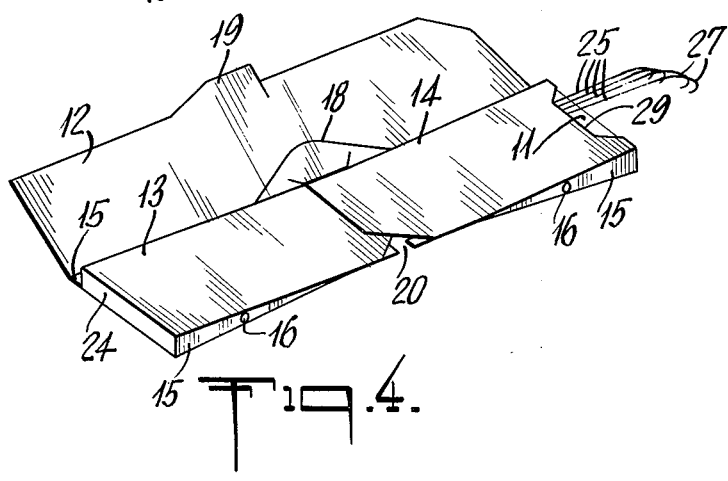

PACKAGE FOR MULTISTRAND SURGICAL SUTURES

BACKGROUND OF THE INVENTION

1. Field of the Invention

The present invention relates to packages for surgical sutures, and more particularly to packages for multiple strands of sutures which allow single strand dispensing.

2. Description of Prior Art

In many surgical procedures, the surgeon employs a large number of sutures in making the wound closure. Suture manufacturers recognized this practice and offer many sutures in multistrand packages. This is a matter of convenience to the surgeons and operating room personnel in that they are required to open fewer packages and the multistrand packages serve to keep individual sutures from becoming scattered during the course of the operation.

One problem associated with multiple suture packaging has been to provide a means for allowing individual sutures to be removed from the packages without entanglement. In other words, the multistrand suture package must provide for single strand dispensing. This characteristic of the package has been obtained heretofore by providing individual compartments within the package for each suture as illustrated for example in U.S. Pat. Nos. 3,857,484 and 3,759,376. An alternative method is to provide a single channel or tube for the length of the sutures as described, for example, in U.S. Pat. Nos. 3,280,971, 3,338,401 and 3,972,418.

The present invention is concerned with multistrand suture packages of a novel type wherein the suture strands are neither placed in individual compartments nor contained in a single channel or tube, but which, nevertheless, allow for single strand dispensing. Moreover, the packages of the present invention are easily loaded by hand or machine and may be used with either needled or unneedled sutures. It is accordingly an object of the present invention to provide a new and improved package for multiple strands of surgical sutures which provides for single strand delivery.

SUMMARY

In accordance with the present invention, packages are provided wherein a plurality of suture strands are maintained within the package as a substantially parallel bundle of filaments wound in the form of a coil comprising a plurality of contiguous, overlapping convolutions with successive convolutions disposed in sequence from one end of the suture to the other and with adjacent convolutions being laterally displaced one from the other.

The desired suture configuration is conveniently obtained by winding the suture bundle about two vertical pins beginning at the bottom of the pins and winding in an upward spiral to provide a plurality of convolutions disposed in sequence over the length of the suture and laterally displaced along the length of the pins with substantially no overlap between adjacent convolutions. The sutures may be wound around the pins as a series of figure eight convolutions, as a series of circular loops, as a series of circular loops having at least one reversal in the direction of winding, or as a combination of these. The wound sutures are maintained in the desired configuration by means of a suture package which is positioned to retain the suture coils before the winding pins are removed.

The suture bundle is maintained within the confines of the suture package with one end of the bundle extending from the package whereby individual sutures may be grasped and withdrawn from the package. The sutures may be multifilament or monofilament, and may have needles attached to the end extending from the package.

The suture package may be formed of paper or plastic or other suitable material and is comprised of at least two panels and means for securing the panels together with the coiled suture bundle positioned therebetween. Particularly preferred is a foldable suture package constructed of a heavy weight, relatively stiff paper or paper board such as 5 point or 12 point sold bleached sulfate board. The panels of such packages may employ integral locking means such as tabs and slots to secure the panels together, or alternatively, adhesive or mechanical e.g., staple fastening means may be used.

DESCRIPTION OF DRAWING

FIG. 1 is a plan view of one preferred suture package for use in the present invention.

FIG. 2 is a view in perspective of the suture package of FIG. 1 positioned over two suture winding pins having a plurality of suture strands wound thereon in a figure eight pattern.

FIG. 3 is a view in perspective of the suture and package of FIG. 2 after the package has been folded to retain the coiled suture between two panels.

FIG. 4 is a view in perspective of the package of FIG. 3 after being removed from the winding pins.

FIG. 5 is a transparent plan view of a suture bundle coiled in the form of multiple figure eight convolutions being laterally displaced in sequence over the length of the suture and retained by a suture package.

FIG. 6 is a view in perspective of two suture winding pins having a bundle of suture strands wound thereon in a circular pattern.

FIG. 7 is a view in perspective of two suture winding pins having a bundle of suture strands wound thereon in a combination of figure eight and circular windings.

DESCRIPTION OF PREFERRED EMBODIMENTS

Suture packages of the present invention are characterized by a plurality of suture strands collated into a bundle of substantially parallel and aligned filaments, and coiled in the form of a series of contiguous, overlapping figure eight or circular convolutions with adjacent convolutions being maintained in sequence over the length of the suture and laterally displaced so that adjacent convolutions are not superimposed directly one upon the other.

The desired suture configuration may be obtained by any convenient method. In a particularly preferred method, the suture bundle is wound around two vertical pins beginning at the bottom of the pins and winding in an upwardly spiraling pattern so that every loop on the pin is above the next preceding loop. In this manner, overlapping of successive suture bundle loops is avoided and, when the pins are removed after means have been provided to maintain the suture loops in their relative positions, the loops are sequentially disposed and laterally displaced or offset one from the other.

The suture strands comprising the bundle are preferably aligned in a substantially parallel manner prior to winding. Parallel alignment insures minimum interference between strands as individual strands are subsequently withdrawn from the bundle within the package. Absolutely parallel alignment, however, is not necessary to obtain individual suture delivery in accordance with the present invention.

The suture package may be of any construction effective to maintain the suture bundle in its desired coiled configuration. Foldable suture packages are most conveniently used since the package may be open during the suture winding operation and then folded about the suture to retain the coiled suture before the supporting winding pins are removed.

Representative figure eight and circular suture configurations and packages of the present invention will be more fully understood by reference to the several drawings which illustrate preferred package designs and a method of winding multistrand sutures to obtain the desired suture coils which allows single strand delivery from a multistrand package in accordance with the present invention.

Turning now to FIG. 1, there is illustrated an open suture package blank adapted for packaging the coiled suture bundles of the present invention. The package is comprised of a foldable paperboard having five main panels identified as suture retaining panels 10 and 11, end panels 13 and 14 and cover panel 12. Panel 10 is foldably attached to panel 11 through gussets 15 which each contain a single circular opening 16. In addition, locking slot 20 is provided on the fold line between panels 10 and 11, locking tab 17 is provided on the outer edge of panel 10.

End panels 13 and 14 are foldably connected to panel 11 through hinge sections 24. Each panel includes a locking tab 22, and 14 additionally contains cutout 21 to provide an opening for removing sutures from the package.

Cover panel 12 is foldably connected to panel 11 through gussets 15. As illustrated, panel 12 contains three package locking slots identified as 18, 19 and 23, the function of which is hereinafter described.

FIG. 2 illustrates the package of FIG. 1 with suture winding pins 26 projecting upward through holes 16 and with suture bundle 25 wound upon pins 16 in an upwardly spiraling figure eight configuration. The individual suture strands forming bundle 25 are in substantially parallel alignment with one another. In winding the suture bundle around pins 26, care is taken to avoid overlapping adjacent suture loops.

FIG. 3 illustrates the suture package of FIG. 2 with the coiled suture retained between panel 11 and end panels 13 and 14 which have been folded inwardly over the suture coil. Tabs 22 of end panels 13 and 14 are locked in slot 23 of panel 12. The ends of suture bundle 25 project from the package through cutout 21 and panel 14.

FIG. 4 illustrates the package of FIG. 3 with panel 10 additionally folded over end panels 13 and 14 and locked in position by means tab 17 being inserted through locking slot 18. The suture bundle projects from the package through cutout 29 in the end section of panel 10. FIG. 4 additionally illustrates needles 27 attached to the individual suture strands comprising bundle 25 and projecting from the package. To complete the package, needles 27 and attached suture are folded back onto the outer surface of panel 10 and covered by panel 12 which folds forward over panel 10 and locks by inserting tab 19 into slot 20, whereby the needled ends of the suture are maintained within the confines of the package.

The configuration of the coiled suture bundle within the package is illustrated by FIG. 5 which shows a three strand suture bundle coiled in accordance with the present invention and retained in a package comprising cover panel 32 heat sealed around peripheral border 30 to backing panel 33 Panel 33 is extended beyond panel 32 and adapted to be folded forward over panel 32 with tab 34 interlocking along edge 28 whereby the ends of sutures 25 are folded back over panel 32 and enclosed within the package. When panel 33 is opened, the ends of sutures 25 are readily available for grasping and individual sutures may be withdrawn from between panels 32 and 33 through opening 35. Openings 31 in heat seal border 30 are openings for the suture winding pins and may be sealed if desired once the pins are removed.

With further reference to FIG. 5, the convolutions of the suture bundle in the packages of the present invention are seen to be contiguous and overlapping, and disposed in sequence from one end of the suture to the other with each convolution being laterally displaced from a superimposed position relative to adjacent convolutions. A unique aspect of the present invention is that while the suture bundle is wound on the winding pins as aforedescribed with care to prevent overlapping of adjacent coils, adjacent convolutions of the suture bundle in the package are contiguous and overlap when the package is removed from the winding pins.

FIG. 6 illustrates winding pins 26 having a bundle of sutures 25 wound in the form of an upwardly spiraling circular coil. For the sake of clarity, the suture folder shown in FIG. 1 is omitted, and the suture coils are spaced apart on the winding pins.

FIG. 7 illustrates a bundle of sutures 25 wound about pins 26 in a combination of circular and crossing coils. As in FIG. 6, the suture folder is omitted and adjacent suture coils are spaced apart for clarity of illustration.

The fabrication of the suture packages of FIG. 5 by heat sealing is well known in the art as described for example in U.S. Pat. No. 3,221,873, which is incorporated herein by reference for its teaching of materials and procedures in this regard. With further reference to FIG. 5, panel 32 is preferably a transparent heat sealable film or laminate while panel 33 is preferably paperboard, having a heat sealable coating thereon. As will be apparent to those skilled in the art, many variations in package design, materials and construction are permissible in providing the packages of the present invention. For example, panels 32 and 33 may be joined by the use of an adhesive applied to the panels in the areas to be joined. The present invention is accordingly not limited by any particular package composition or structure.

The coiled structure within the package of the present invention is characterized by comprising a plurality of sutures strands in substantially parallel alignment and wound in the form of a coil comprising a series of contiguous, overlapping figure eight or circular convolutions, each convolution being laterally displaced from adjacent convolutions and disposed in sequence from one end of the suture to the other. The lateral displacement of the overlapping suture coil convolutions in accordance with the present invention distinguishes the sutures coiled in accordance with the present invention from similar packages wherein adjacent suture coil convolutions are superimposed one upon the other as described, for example, for a single suture in U.S. Pat. No. 3,444,994.

Sutures packaged in bundles of 3 to 8 strands or more may be individually removed from the packages of the present invention by simply grasping an exposed end of a single suture and withdrawing the suture with a steady pull. The unique winding of the suture bundle within the package allows individual suture strands to be withdrawn from the bundle without entangling the sutures remaining in the package.

Sutures packaged in accordance with the present invention may be multifilament or monofilament sutures and multifilament sutures may be braided, twisted or covered. In addition, these sutures may be packaged with or without needles attached to the end of the suture which extends from the package and is intended to be grasped in order to withdraw the suture from the package.

While the foregoing has described a package construction and method for winding and loading sutures into the package in accordance with a preferred embodiment of the present invention, many variations will be apparent to those skilled in the art. For example, the sutures may be wound on any apparatus which will provide the suture coil configuration illustrated in FIGS. 5 – 7. Once so wound, the suture may be loaded into any package which will effectively maintain the suture in the desired configuration and provide access to one end of the suture bundle to permit withdrawal of individual sutures from the package.

I claim

1. A multistrand suture package providing individual suture delivery comprising a plurality of suture strands in substantially parallel alignment, said suture strands being wound in the configuration of a coil comprising a series of convolutions disposed in sequence from one end of the suture to the other with each convolution being laterally displaced from adjacent convolutions, and retaining means holding the wound suture strands in the aforesaid configuration with one end of said suture strands extending from said retaining means, whereby individual suture strands may be grasped and withdrawn from said retaining means, without entangling sutures remaining in the package.

2. A package of claim 1 wherein said suture strands are wound in the form of a coil comprising a series of figure eight convolutions.

3. A package of claim 1 wherein said suture strands are wound in the form of a coil comprising a series of circular convolutions.

4. A package of claim 1 wherein said suture strands are wound in the form of a coil comprising a series of circular convolutions having at least one reversal in the direction of winding.

5. A package of claim 1 wherein said suture strands have needles attached to the end extending from said retaining means.

6. A package of claim 1 comprising a plurality of multifilament braided suture strands.

7. A package of claim 6 wherein said suture strands have needles attached.

8. A package of claim 1 wherein said retaining means comprise first and second panels foldably connected and adapted to hold the suture coil therebetween when said panels are in a folded position, and means associated with said panels for holding said panels in said folded position.

9. A suture package according to claim 8 wherein the means for holding said panels in a folded position comprise a locking tab along a free edge of one panel which enters into alignment with and engages a locking slot in the other panel when said panels are in a folded position.

10. A suture package according to claim 8 wherein the means for holding said panels in a folded position comprise stapling means.

11. A suture package according to claim 8 wherein the means for holding said panels in a folded position comprise adhesive means.

12. A package of claim 8 wherein the ends of the suture strands extending from the retaining means extend from between said first and second panels and are returned back over said second panel, and said package additionally comprises a third panel foldably attached to said first panel and adapted to be folded down over said suture ends to retain said ends in the aforesaid position over said second panel, and means associated with said third panel for holding said panel in said folded position.

13. A package of claim 12 wherein said suture strands have needles attached to the ends retained by said third panel.

14. A package of claim 1 wherein said retaining means comprise a first rectangular panel having major and minor edges, second and third panels foldably connected to said first panel along the minor edges thereof, and a fourth panel foldably connected to said first panel along one major edge thereof, said second and third panels being adapted to fold inwardly over said first panel with said suture strands retained therebetween, and said fourth panel being adapted to fold over said second and third panel, and means for holding said panels in the aforesaid folded positions.

15. A package of claim 14 wherein said second and third panels have locking tabs and said first panel has a locking slot, said tabs and slot entering into alignment and engaging one another when said second and third panels are folded over said first panel.

16. A package of claim 14 wherein said fourth panel has a locking tab and said first panel has a locking slot, said tab and slot entering into alignment and engaging one another when said fourth panel is folded over said second and third panels.

17. A package of claim 1 wherein said retaining means comprises first and second panels having the suture coil positioned therebetween, said panels being joined around the periphery of said suture coil in a border containing an opening with the suture strands extending therefrom.

18. A package of claim 17 wherein said first and second panels are joined by a heat seal.

19. A package of claim 17 wherein said first and second panels are joined by an adhesive.

* * * * *

UNITED STATES PATENT AND TRADEMARK OFFICE
CERTIFICATE OF CORRECTION

PATENT NO. : 4,089,409
DATED : May 16, 1978
INVENTOR(S) : Robert J. Cerwin

It is certified that error appears in the above-identified patent and that said Letters Patent are hereby corrected as shown below:

At Column 4, Line 54, "the coiled structure" should be
-- the coiled suture --.
In Claim 1, Column 5, Line 34, "series of convolutions" should be -- series of contiguous, overlapping convolutions --.
In Claim 1, Column 5, Line 36, "laterally displaced from adjacent" should be -- laterally displaced from a superimposed position relative to adjacent --.

Signed and Sealed this

Nineteenth Day of September 1978

[SEAL]

Attest:

RUTH C. MASON
Attesting Officer

DONALD W. BANNER
Commissioner of Patents and Trademarks